(12) United States Patent
Stepp

(10) Patent No.: US 10,468,868 B2
(45) Date of Patent: Nov. 5, 2019

(54) POWER CONTROL UNIT WITH REMOTE SENSOR

(71) Applicant: Patrick Stepp, Dunkirk, MD (US)

(72) Inventor: Patrick Stepp, Dunkirk, MD (US)

( * ) Notice: Subject to any disclaimer, the term of this patent is extended or adjusted under 35 U.S.C. 154(b) by 920 days.

(21) Appl. No.: 14/990,445

(22) Filed: Jan. 7, 2016

(65) Prior Publication Data

US 2016/0197467 A1 Jul. 7, 2016

Related U.S. Application Data

(60) Provisional application No. 62/100,719, filed on Jan. 7, 2015.

(51) Int. Cl.
| | |
|---|---|
| *H02H 3/08* | (2006.01) |
| *G01N 31/00* | (2006.01) |
| *H01H 35/24* | (2006.01) |
| *H04Q 9/00* | (2006.01) |
| *G01P 13/00* | (2006.01) |
| *H02H 5/08* | (2006.01) |
| *G01F 1/075* | (2006.01) |

(52) U.S. Cl.
CPC ............... *H02H 3/08* (2013.01); *G01N 31/00* (2013.01); *G01P 13/004* (2013.01); *G01P 13/0006* (2013.01); *H01H 35/24* (2013.01); *H02H 5/08* (2013.01); *H04Q 9/00* (2013.01); *G01F 1/075* (2013.01); *H04Q 2209/40* (2013.01)

(58) Field of Classification Search
None
See application file for complete search history.

(56) References Cited

U.S. PATENT DOCUMENTS

2010/0085211 A1* 4/2010 Wang ................. G01F 1/10
340/870.02

\* cited by examiner

*Primary Examiner* — Thienvu V Tran
*Assistant Examiner* — David M Stables
(74) *Attorney, Agent, or Firm* — Tanner IP, PLLC

(57) ABSTRACT

An electrical control system may include a sensor unit with an attachment mechanism for mounting the sensor unit to a fluid pipe, a fluid flow sensor, and a signal generator configured to generate a signal indicating at least one of whether the flow sensor detects a fluid flow in the fluid pipe or whether the flow sensor detects no fluid flow in the fluid pipe. The system may also include a control unit having one or more of an electrical plug, an electrical socket, an interruptible circuit between the electrical plug and the electrical socket, a receiving device configured to receive the signal from the sensor unit, and a processor configured to interrupt the circuit between the electrical plug and the electrical socket based on at least one of receipt of the signal or interruption of the signal.

18 Claims, 4 Drawing Sheets

POWER CONTROL UNIT WITH REMOTE SENSOR

RELATED APPLICATIONS

This application claims priority under 35 U.S.C. 119 to U.S. Provisional Application Ser. No. 62/100,719 filed Jan. 7, 2015, entitled "POWER CONTROL UNIT WITH REMOTE SENSOR," the entire contents of which are hereby incorporated by reference for all purposes.

BACKGROUND

The present invention generally relates to means for controlling the electrical power provided to various appliances and equipment based on readings and/or control signals from remote sensors.

SUMMARY

According to first aspects of the invention, an electrical control system may include a sensor unit with an attachment mechanism for mounting the sensor unit to a fluid pipe, a fluid flow sensor, and a signal generator configured to generate a signal indicating at least one of whether the flow sensor detects a fluid flow in the fluid pipe or whether the flow sensor detects no fluid flow in the fluid pipe. The system may also include a control unit having one or more of an electrical plug, an electrical socket, an interruptible circuit between the electrical plug and the electrical socket, a receiving device configured to receive the signal from the sensor unit, and a processor configured to interrupt the circuit between the electrical plug and the electrical socket based on at least one of receipt of the signal or interruption of the signal.

In embodiments, the fluid flow sensor may include a plurality of permanent magnets and an induction coil.

In embodiments, the attachment mechanism may include a flange integrally attached to the sensor unit, a gasket and a plurality of clamps configured to fit around the pipe.

In embodiments, the sensor unit may be configured to transmit the signal via at least one of a wire connected to the sensor unit or via a wireless communication channel.

In embodiments, the control unit may be further configured to send a signal to a remote device when the circuit is interrupted by the control unit.

According to further aspects of the invention, an electrical control system may include a sensor unit with a sensor and a signal generator configured to generate a signal based at least in part on readings of the sensor. Systems may also include a control unit having one or more of an electrical input, an electrical output, an interruptible circuit between the electrical input and the electrical outlet, a receiving device configured to receive the signal from the sensor unit, and a mechanism configured to interrupt the circuit between the electrical input and the electrical outlet based on at least one of receipt of the signal or interruption of the signal.

In embodiments, the sensor may include at least one of a flow sensor, a current sensor, a pH sensor, a pressure sensor, and/or a vacuum sensor.

In embodiments, the sensor and the control unit may be configured to communicate via a wireless network.

In embodiments, the electrical input may include a standard electrical plug, such as a Type A or Type B connector, and the electrical outlet may include a corresponding standard electrical receptacle.

In embodiments, the control unit may be further configured to send a signal to a remote device when the circuit is interrupted by the control unit.

According to further aspects of the invention, a control unit may be provided including an electrical plug, an electrical receptacle, an interruptible circuit between the electrical plug and the electrical receptacle, a receiving device configured to receive the signal from a remote sensor unit, and/or a processor configured to interrupt the circuit between the electrical plug and the electrical receptacle based on at least one of receipt of the signal or interruption of the signal.

In embodiments, the remote sensor may include at least one of a flow sensor, a current sensor, a pH sensor, a pressure sensor, and/or a vacuum sensor.

In embodiments, the control unit may be configured to communicate with the remote sensor via a wireless network.

In embodiments, the electrical input may include a standard electrical plug, such as a Type A or Type B connector, and the electrical outlet may include a corresponding standard electrical receptacle.

In embodiments, the control unit may be further configured to send a signal to a remote device when the circuit is interrupted by the control unit.

According to further aspects of the invention, a sensor unit may be provided including one or more of an attachment mechanism, e.g. for mounting the sensor unit to a fluid pipe, a sensor configured to contact fluid in the pipe when the sensor unit is mounted to the pipe, and a signal generator configured to generate a signal based at least in part on readings of the sensor. In some examples, the sensor may include at least one of a flow sensor, a current sensor, a pH sensor, a pressure sensor, and/or a vacuum sensor.

In embodiments, the sensor may include at least a flow sensor, and the signal may indicate at least one of whether the flow sensor detects a fluid flow in the pipe or whether the flow sensor detects no fluid flow in the pipe.

In embodiments, the sensor unit may be configured to communicate with a control unit via a wireless network.

In embodiments, the sensor unit may be configured to mount to the pipe via a circular hole drilled in the pipe.

In embodiments, the sensor unit may include a charger electrically connected to at least one of a battery or a capacitor.

In embodiments, the sensor unit may be at least partially user programmable, e.g. to set parameters by which the signal is generated or interrupted.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention claimed. The detailed description and the specific examples, however, indicate only preferred embodiments of the invention. Various changes and modifications within the spirit and scope of the invention will become apparent to those skilled in the art from this detailed description.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the related technology. No attempt is made to show structural details of technology in more detail than may be necessary for a fundamental understanding of the invention and various ways in which it may be practiced. In the drawings.

DETAILED DESCRIPTION OF THE INVENTION

Figure 1:
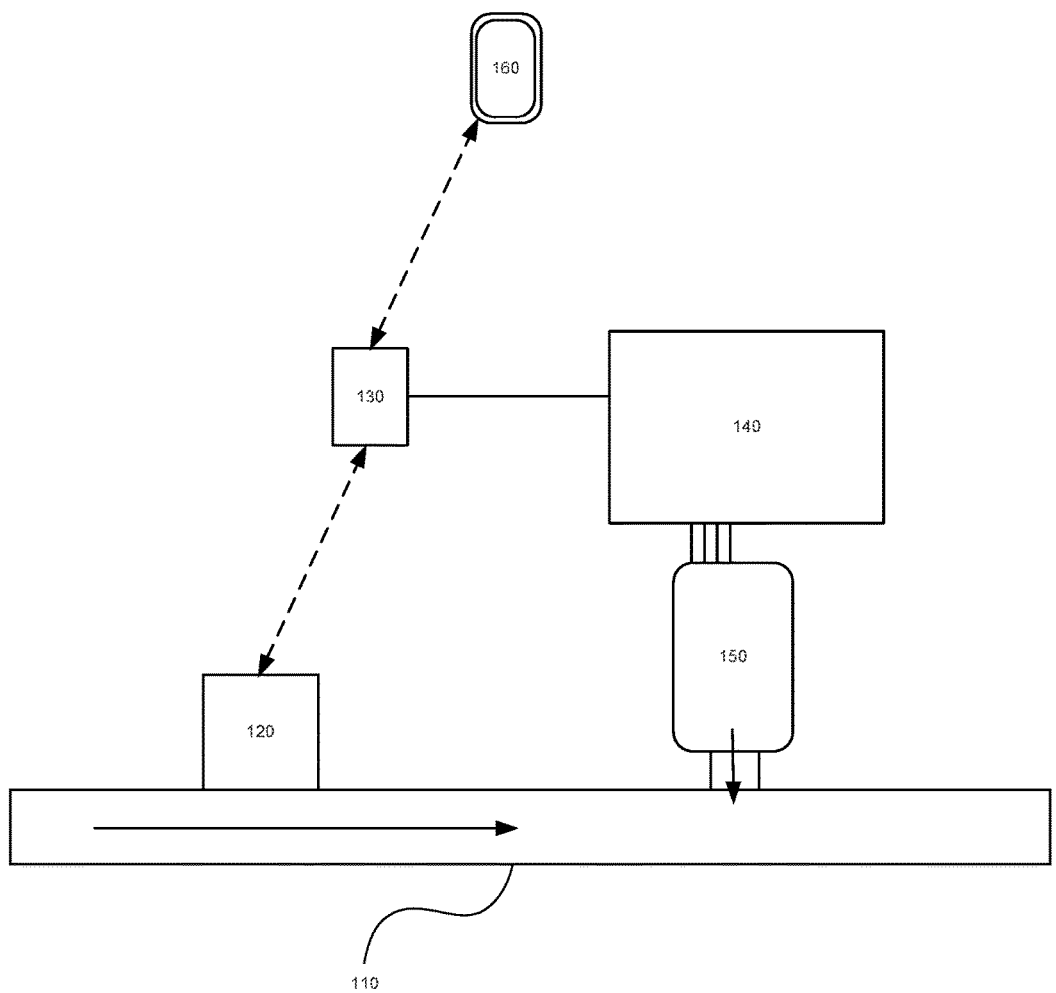
FIG. 1 is a schematic diagram of a flow sensor and control arrangement according to aspects of the invention.

It is understood that the invention is not limited to the particular methodology, protocols, etc., described herein, as these may vary as the skilled artisan will recognize. It is also to be understood that the terminology used herein is used for the purpose of describing particular embodiments only, and is not intended to limit the scope of the invention. It also is to be noted that as used herein and in the appended claims, the singular forms "a," "an," and "the" include the plural reference unless the context clearly dictates otherwise. Thus, for example, a reference to "a sensor" is a reference to one or more sensors and equivalents thereof known to those skilled in the art.

Unless defined otherwise, all technical terms used herein have the same meanings as commonly understood by one of ordinary skill in the art to which the invention pertains. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law.

FIG. 1 is a schematic diagram showing an exemplary layout including a sensor and control unit system according to aspects of the invention. In the example shown in FIG. 1, a pipe 110 may be, for example, a water pipe connected to a swimming pool. However, it should be appreciated that the example shown in FIG. 1, and other examples described herein, is only one implementation, among many, in which aspects of the invention may be used. A sensor 120 is connected to pipe 110 such that flow or other characteristics/conditions inside of the pipe 110 may be monitored. Sensor 120 is also configured to communicate with a control unit 130. The communication may be performed, for example, using communication wires, power wires, or by various wireless technologies, such as Bluetooth, WiFi, LAN, WAN or other means. In some examples, control unit 130 may be configured to plug into an electrical outlet, and to have power cords from one or more other devices plugged into the control unit. These may include, for example, standard 2 or 3 prong household outlets and plugs, industrial and multiphase outlets and corresponding plugs, hard-wired points, etc. The control unit 130, in a basic form, acts as a power bridge between a power outlet and a device that is plugged into the control unit. In the example shown in FIG. 1, a device 140 is plugged into control unit 130 and relies on control unit 130 to provide electrical power from an outlet to the device. The device 140 may be, for example, a pump connected to chemical tank 150 that adds chemicals to the water supply flowing in pipe 110, or any other type of device that may be advantageously disabled under certain conditions sensed by sensor 120.

Some examples of how the system in FIG. 1 may be employed are in the context of water supply systems that routinely add chemicals, such as chlorine to a pool water supply. In such cases, if the flow of water in pipe 110 stops, there can be health risks associated with continuing to add the chemical(s), e.g. building up a dangerous chemical concentration in a small volume of stagnated water. Therefore, the sensor 120 may be configured to detect the flow of water in pipe 110, and to send a signal to control unit 130 while the flow is active and/or if the flow stops. The control unit 130 may be configured to interrupt the power to device 140 if the signal indicates that the flow in pipe 110 has stopped, and/or if a signal that indicates positive flow is not received.

It is envisioned that the present subject matter may find applicability in a wide variety of contexts in which the benefits of constant or near constant industrial monitoring are not available, e.g. in household or small business environments. Therefore, another aspect of the invention may include communication between control unit 130 and a remote device 160, such as a smartphone, smart watch, a tablet computer, etc. This communication link may be provided using various combinations of communication wires, power wires, or various wireless technologies known in the art, such as Bluetooth, WiFi, LAN, WAN or other means. In some examples, the control unit 130 and/or sensor unit 120 may be programmable via an application running on portable computing device, such as remote device 160. Such programming may include parameters by which signals are generated and/or interrupted by the sensor unit 120, and/or parameters by which the control unit interrupts the electrical circuit to device 140. It should be appreciated that the sensor unit 120 may be configured to set a binary signal (e.g. there is or is not a flow), or it can be programmed to send more detailed information (such as rate of flow, pH, etc.) by which logic onboard the control unit 130 may determine whether certain control parameters are met. In some examples, the sensor unit itself may be programmed to read non-binary sensor data and to generate or interrupt the signal to control unit 130 based on comparing the non-binary sensor readings to programmed parameters.

In some examples, the system may be configured to send an alert to remote device 160 (via SMS message, Bluetooth signal, or various other addressing methods) if the flow in pipe 110 stops, or other condition(s) are met that interrupt the power being provided to device 140. In this manner, the user of a household system or small business can be quickly and easily alerted to the problem state and can resolve the problem.

In some examples, since control unit 130 is plugged in to a power outlet, it has all the power necessary to maintain and/or perform intermittent communication with sensor 120 and/or remote device 160. Control unit 130 may also be configured to provide low-current power to sensor 120, e.g. via additional power outlets and/or wires. However, in some cases sensor 120 may be battery powered, self-powered, etc.

In some examples, control unit 130 may also be configured to report to remote device 160 if device 140 is not drawing power, e.g. if the device 140 has shut down due to a malfunction or other control such as running out of chemical in tank 150.

Additional non-limiting examples of sensors and control modules according to aspects of the invention are discussed further below with reference to FIGS. 2-7.

Figure 2:
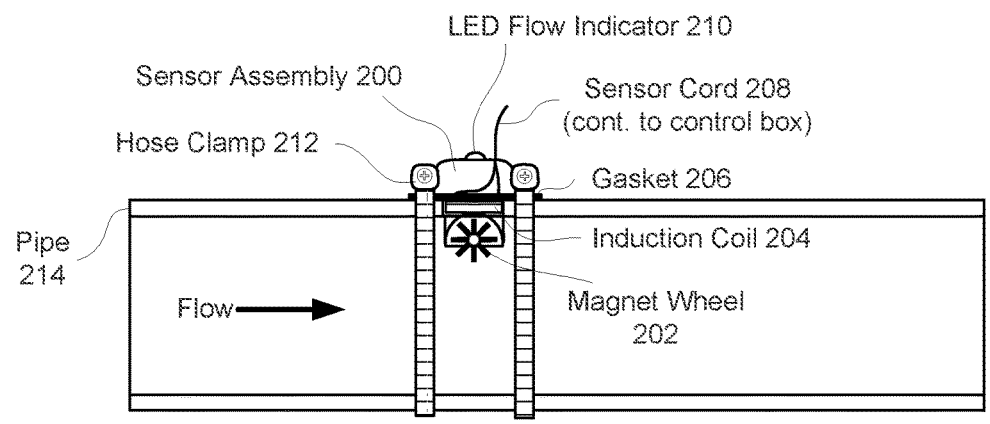
FIG. 2 is a schematic diagram of a flow sensor arrangement according to aspects of the invention.

FIG. 2 is a schematic diagram of a flow sensor arrangement according to aspects of the invention. As shown in FIG. 2, a sensor assembly 200 including a "paddle wheel" of permanent magnets 202 and an induction coil 204 may be partially inserted through a pipe 214 and clamped to the pipe via hose clamps 212 or other means. A gasket 206 around a flange of the sensor assembly 200 may provide a watertight seal between the sensor assembly and the hole in the pipe 214. Rotation of the magnets 202 may be caused by water flow in the pipe 214 and may generate a signal from the sensor assembly 200 via the induction coil 204 proximate to the permanent magnets 202. As shown in FIG. 2, the signal may be carried over an electrical line 208 to the control unit, or it may be transmitted wirelessly. It should be noted that the output from the sensor assembly 200 may be configured in various ways. For example, a positive flow condition may result in a constant or intermittent signal, the interruption of which can signal a stop in the flow. In some examples, the steady signal may be fully or partially powered by the induction coil 204. In some examples, a stop in the flow may initiate an independent signal that alerts the control unit. For example, the sensor assembly 200 may have control logic, and a battery, capacitor or other power source in the housing, that responds to the absence of current from the induction coil 204 by initiating a signal. In some examples, the induction coil 204 may be used to charge a battery or capacitor in the housing that are used to power the alert signal.

The sensor assembly 200 in FIG. 2 may also include a LED, sound, or other indicator 210 used to support visual or manual inspection, e.g. that lights when flow is detected, that sounds when flow is not detected, and/or changes color, illumination, sound, etc. when the sensor detects a change in flow.

Figure 3:
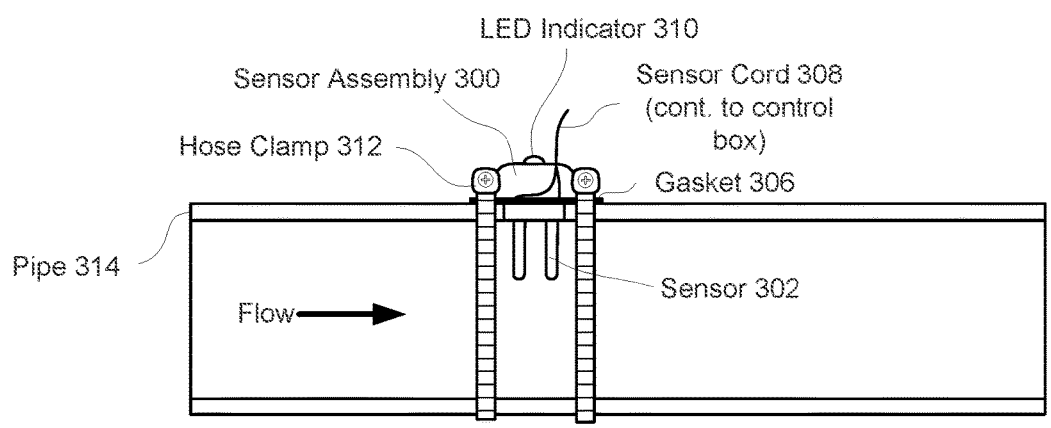
FIG. 3 is a schematic diagram of an electrical current sensor arrangement according to aspects of the invention.

FIG. 3 is a schematic diagram of multi-purpose sensor assembly 300 according to aspects of the invention. As shown in FIG. 3, a sensor assembly 300 including one or more sensor probes 302 may be partially inserted through a pipe 314 and clamped to the pipe via hose clamps 312 or other means. It is noted that the interface between the sensor assembly 300 and the pipe 314 may be standardized such that various sensors can be attached using the same dimension hole or other mounting scheme. A gasket 306 around a flange of the sensor assembly 300 may provide a watertight seal between the sensor assembly 300 and the hole in the pipe 314. The sensor probes 302 inserted into the pipe, or otherwise positioned to detect the desired condition, may be configured, for example, to detect electrical current, temperature, pH, or various other conditions that may be relevant to the operation of another device such as shown in FIG. 1. For example, if a heater or other device is malfunctioning, the sensor in FIG. 3 may be used as an additional safeguard to shut down the device even when the device's own safeguards are not working. As shown in FIG. 3, the signal may be carried over an electrical line 308 to the control unit, or it may be transmitted wirelessly. It should be noted that the output from the sensor assembly 300 may be configured in various ways, depending on the condition(s) that are being sensed. For example, an electrical current, pH, or chemical level, above a certain threshold may initiate an independent signal that alerts the control unit, or the signal may include non-binary information that is constantly, or periodically, transmitted to the control unit.

The sensor assembly 300 in FIG. 3 may also include a LED, sound, or other indicator 310 used to support visual or manual inspection, e.g. that lights when current is detected, that sounds when a certain pH level or range is detected, and/or changes color, illumination, sound, etc. when the sensor detects a change in relevant condition.

Figure 4:
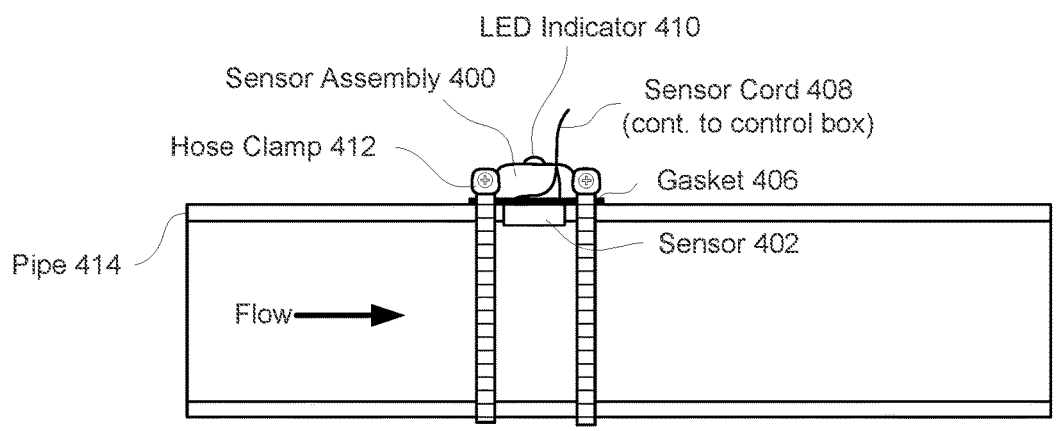
FIG. 4 is a schematic diagram of a pressure/vacuum sensor according to aspects of the invention.

FIG. 4 is a schematic diagram of a pressure/vacuum sensor assembly 400 according to aspects of the invention. As shown in FIG. 4, a sensor assembly 400 including one or more pressure/vacuum sensors 402 may be partially inserted through a pipe 414 and clamped to the pipe via hose clamps 412 or other means. As previously mentioned, the interface between the sensor assembly 400 and the pipe 414 may be standardized such that various sensors can be attached using the same dimension hole or other mounting scheme. A gasket 406 around a flange of the sensor assembly 400 may provide a watertight seal between the sensor assembly 400 and the hole in the pipe 414. As shown in FIG. 4, the pressure/vacuum signal may be carried over an electrical line 408 to the control unit, or it may be transmitted wirelessly. The sensor assembly 400 may be configured to send the signal when the pressure/vacuum meets certain criteria and/or the signal may include specific pressure/vacuum information that is constantly, or periodically, transmitted to the control unit.

It is noted that any of the sensor units described above can include programmable logic, e.g. on a storage device, by which a user can set parameters of the sensor such as ranges or thresholds for sending alert signals to the control unit, signal timing, wireless communication address and/or synchronization information, etc.

Figure 5:
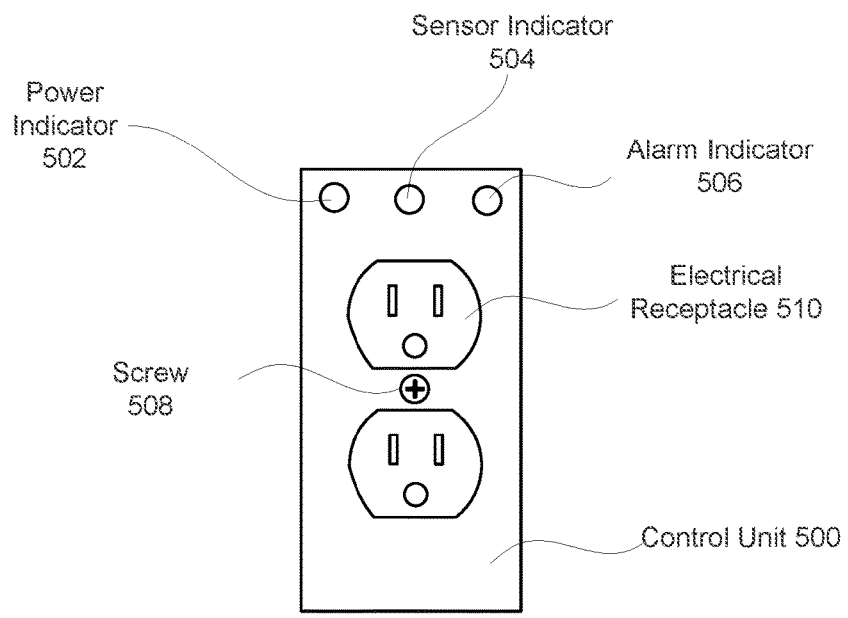
FIG. 5 is a schematic diagram of a control unit according to aspects of the invention.

FIG. 5 is a front schematic diagram of a control unit according to aspects of the invention. As shown in FIG. 5, the control unit 500 may include a standard electrical receptacle 510 that receives, for example, 2 or 3-prong electrical plugs such as Type A and/or Type B connectors. A plurality of visual or other indicators may be included, e.g. an LED power indicator 502 indicating that the control unit is receiving power, an LED sensor indicator 504 indicating that the control unit is coupled to a sensor unit, an LED alarm indicator 506 indicting that the internal circuit has been interrupted, etc. The control unit 500 may be configured to plug into a standard receptacle, similar to the electrical receptacle 510 that is on the face of the control unit. However, in some embodiments, a control unit may be hard-wired to an electrical power line (e.g. as a replacement wall receptacle) and/or to a device (e.g. permanently connected to the power supply line of the device). Screw 508 may be configured to penetrate the control unit 500 for attachment to a corresponding hole in a wall receptacle.

Figure 6:
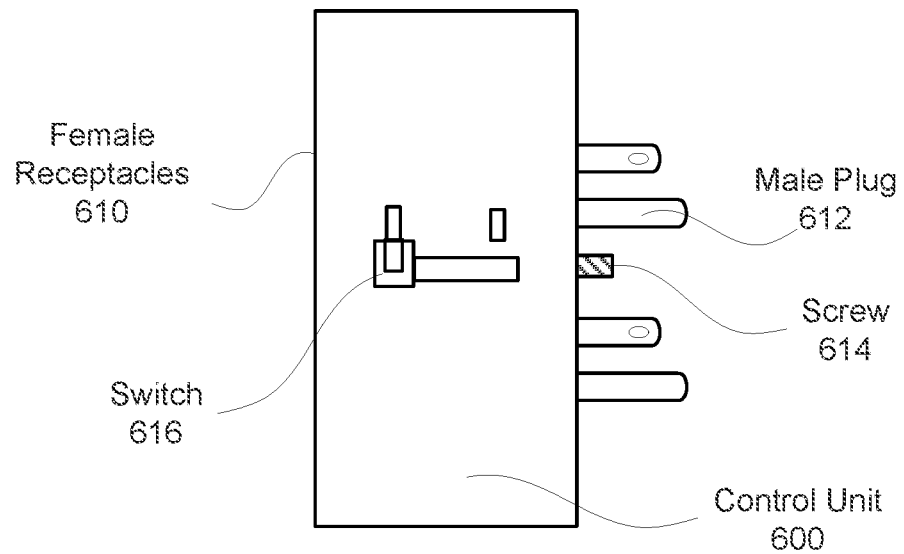
FIGS. 6 and 7 are side views of a control unit according to aspects of the invention.
Figure 7:
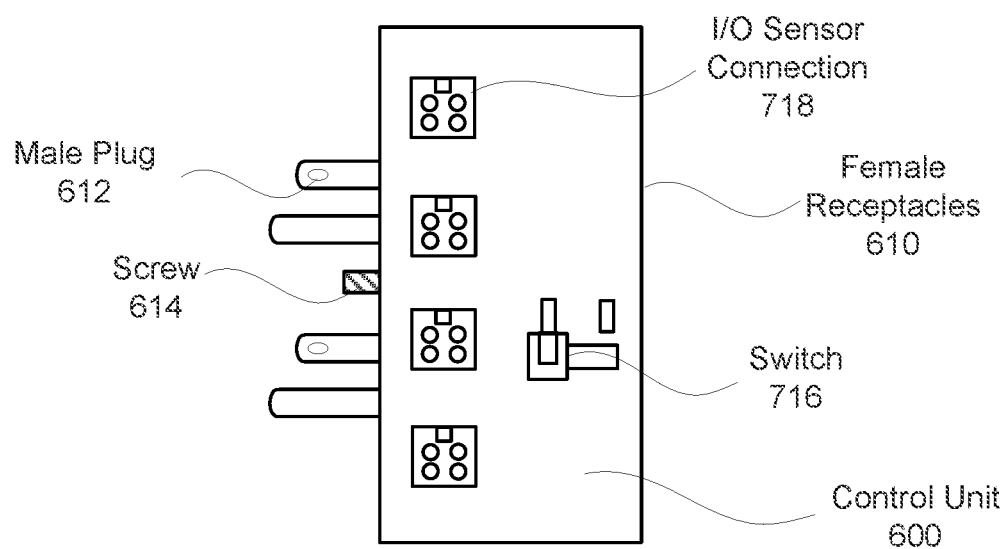

FIGS. 6 and 7 are side views of a control unit according to aspects of the invention. As shown in both of these figures, the control unit 600 may include standard electrical plugs 612, e.g. extending from the back surface of the control unit 600. Inside of the control unit 600, an interruptible electrical circuit may be provided between the plugs 612 shown in FIGS. 6 and 7, and the female receptacles 610 and/or the receptacles 510 shown in FIG. 5. The means by which the circuit(s) are interruptible may take various forms including electrically powered switching elements, breakers, etc. In some examples, the control unit 600 may include a manual switch 616 that disposes the control unit in either of a normally open or normally closed configuration. As such, it may also be possible for the control unit 600 to maintain an interrupted (off) state until a signal is received and/or threshold is detected, and then close the circuit to an "on" state based on the signal or threshold. Such modifications may be advantageous, for example, when a device should be turned on only under certain circumstances, such as a sump flood, etc.

Individual control units may also include multiple sensor inputs and/or channels by which the control unit can communicate with multiple sensor units. For example, as shown in FIG. 7, the control unit may include a plurality (in this case 4) sensor input/power connections 718 with a standardized interface for connecting similar or dissimilar sensors units to the control unit. One or more manual switches 716 may also be provided that alter a configuration associated with one or more of the sensor input/power connections 718. For example, the switch 716 may alter a mode of the I/O such that a signal activates or deactivates a receptacle 610, it may turn output power to one or more of the sensor input/power connections 718 on or off, etc.

The control units shown in FIGS. 5-7 may include various programmable logic, e.g. on a storage device, by which a user can set parameters regarding any of the sensor units coupled to the control unit, ranges or thresholds for interrupting the internal circuit, query timing, wireless communication address and/or synchronization information, etc.

In some examples, the control unit shown in FIGS. 5-7 may also include a wireless communication device by which the control unit can communicate with sensor units and/or with a remote device such as 160 shown in FIG. 1. The control unit may be configured to transmit an alert to such a remote device when a circuit is interrupted and/or is closed based on sensor information as described herein.

In some examples, the control unit, sensors, and/or cables may be watertight and/or resistant to chemicals, humidity, and may be configured/constructed to operate in extreme temperatures, e.g. ranging from 0° F. to 140° F., or as otherwise required.

Although configurations using standard household electrical connections have been described, it should be understood that the invention is not limited to such configurations, and that control units can be, for example, enlarged and/or expanded for new and specialty installations and/or hard wire installs.

Additional sensors that detect, for example, water, light, sound, UV and/or IR light, radar, Bluetooth, Wi-Fi, etc. can be implemented with a control unit as described herein. The sensor must simply generate an I/O signal and may be powered by the control unit (e.g. 12 or 24 VAC/VDC). Likewise, additional electronics can be installed in the sensor unit to accommodate various control unit designs such as described herein.

In some examples, the control unit and/or sensor units may be made from ABS or other plastic and may be be designed as not to require additional bonding and/or grounding devices or connections.

In some examples, sensor cables may be be shielded from external EMP/EMF according to specific requirements.

While various embodiments have been described above, it is to be understood that the examples and embodiments described above are for illustrative purposes only and that various modifications or changes in light thereof will be suggested to persons skilled in the art, and are to be included within the spirit and purview of this application and scope of the appended claims. Therefore, the above description should not be understood as limiting the scope of the invention as defined by the claims.

What is claimed is:

1. An electrical control system, comprising:
   a sensor unit including an attachment mechanism for mounting the sensor unit to a fluid pipe, a fluid flow sensor, and a signal generator configured to generate a signal indicating at least one of whether the flow sensor detects a fluid flow in the fluid pipe or whether the flow sensor detects no fluid flow in the fluid pipe;
   a control unit including
      an electrical plug;
      an electrical socket;
      an interruptible circuit between the electrical plug and the electrical socket;
      a receiving device configured to receive the signal from the sensor unit; and
      a processor configured to interrupt the circuit between the electrical plug and the electrical socket based on at least one of the signal or interruption of the signal,
   wherein the fluid flow sensor includes a plurality of permanent magnets and an induction coil.

2. The control system of claim 1, wherein the sensor unit is configured to transmit the signal via at least one of a wire connected to the sensor unit or via a wireless communication channel.

3. The control system of claim 1, wherein the control unit is further configured to send an alert signal to a remote user device when the circuit is interrupted by the control unit.

4. The control system of claim 1,
   wherein the sensor unit further includes an additional sensor including at least one of a current sensor, a pH sensor, a chemical sensor, a pressure sensor, or a vacuum sensor, and
   wherein the signal generator is further configured to communicate information to the control unit based at least in part on readings of the additional sensor reflecting a condition within the fluid pipe.

5. The control system of claim 1, wherein the sensor unit includes a charger electrically connected to at least one of a battery or a capacitor, the charger configured to generate an electrical current via the flow sensor, and the signal generator configured to generate the signal using an electrical potential stored in the at least one of a battery or capacitor.

6. The control system of claim 1, wherein the sensor unit is user programmable to set parameters for at least one of sending the signal or interrupting the signal.

7. An electrical control system, comprising:
   a sensor unit including an attachment mechanism for mounting the sensor unit to a fluid pipe, a fluid flow sensor, and a signal generator configured to generate a signal indicating at least one of whether the flow sensor detects a fluid flow in the fluid pipe or whether the flow sensor detects no fluid flow in the fluid pipe;
   a control unit including
      an electrical plug;
      an electrical socket;
      an interruptible circuit between the electrical plug and the electrical socket;
      a receiving device configured to receive the signal from the sensor unit; and a processor configured to interrupt the circuit between the electrical plug and the electrical socket based on at least one of the signal or interruption of the signal, wherein the attachment mechanism includes a flange integrally attached to the sensor unit, a gasket and a plurality of clamps configured to fit around the pipe.

8. An electrical control system, comprising:

a sensor unit including a sensor and a signal generator configured to generate a signal based at least in part on readings of the sensor; and a control unit including an electrical input;

an electrical output;

an interruptible circuit between the electrical input and the electrical outlet;

a receiving device configured to receive the signal from the sensor unit; and a mechanism configured to interrupt the circuit between the electrical input and the electrical outlet based on at least one of the signal or interruption of the signal, wherein the sensor includes at least one of a flow sensor, a pH sensor, a chemical sensor, a pressure sensor, or a vacuum sensor, and wherein the electrical input includes at least one of a Type A electrical plug or a Type B electrical plug, and the electrical output includes a corresponding standard electrical socket.

9. The control system of claim 8, wherein the sensor includes at least one of a pH sensor, or a chemical sensor.

10. The control system of claim 8, wherein the sensor unit and the control unit are configured to communicate via a wireless network.

11. The control system of claim 8, wherein the control unit is further configured to send an alert signal to a remote user device when the circuit is interrupted by the control unit.

12. The control system of claim 8, wherein the signal indicates at least one of whether the sensor detects a fluid flow in the pipe or whether the sensor detects no fluid flow in the pipe.

13. The control system of claim 8, wherein the sensor unit is configured to mount to a pipe via a circular hole drilled in the pipe.

14. The control system of claim 8, wherein the control unit is user programmable to set parameters for interrupting the circuit, and the control unit is configured to apply information included in the signal to the parameters in determining whether to interrupt the circuit.

15. An electrical control unit, comprising:

an electrical plug;

an electrical receptacle;

an interruptible circuit between the electrical plug and the electrical receptacle;

a receiving device configured to receive a signal from a remote sensor unit; and a processor configured to interrupt the circuit between the electrical plug and the electrical receptacle based on at least one of information included in the signal or interruption of the signal, wherein the processor is user programmable to set parameters for interrupting the circuit, and the processor is configured to apply the at least one of information included in the signal or interruption of the signal to the parameters in determining whether to interrupt the circuit, and wherein the electrical plug includes at least one of a Type A electrical plug or a Type B electrical plug, and the electrical receptacle includes a corresponding standard electrical socket.

16. The control unit of claim 15, wherein the remote sensor unit includes at least one of a flow sensor, a pH sensor, a chemical sensor, a pressure sensor, or a vacuum sensor.

17. The control unit of claim 15, wherein the control unit is configured to communicate with the remote sensor via a wireless network.

18. The control unit of claim 15, wherein the control unit is further configured to send an alert signal to a remote user device when the circuit is interrupted by the control unit.

* * * * *